(12) United States Patent
Rao et al.

(10) Patent No.: US 6,472,574 B2
(45) Date of Patent: Oct. 29, 2002

(54) PRODUCTION OF 1,2-DIHYDRO AND 2,2-DIHYDRO HEXAFLUOROPROPANES AND AZEOTROPES THEREOF WITH HF

(75) Inventors: Velliyur Nott Mallikarjuna Rao, Wilmington; Francis John Walczak, New Castle, both of DE (US)

(73) Assignee: E. I. du Pont Nemours and Company, Wilmington, DE (US)

( * ) Notice: Subject to any disclaimer, the term of this patent is extended or adjusted under 35 U.S.C. 154(b) by 0 days.

(21) Appl. No.: 10/096,295

(22) Filed: Mar. 11, 2002

(65) Prior Publication Data

US 2002/0128526 A1 Sep. 12, 2002

Related U.S. Application Data

(62) Division of application No. 09/445,742, filed as application No. PCT/US95/05862 on May 19, 1995, now Pat. No. 6,388,147.

(51) Int. Cl.$^7$ ............................................... C07C 17/08
(52) U.S. Cl. ....................... 570/164; 570/166; 570/168; 570/172
(58) Field of Search ................................ 570/164, 166, 570/168, 172

(56) References Cited

U.S. PATENT DOCUMENTS

| | | |
|---|---|---|
| 3,541,165 A | 11/1970 | Vecchio |
| 3,632,834 A | 1/1972 | Christoph, Jr. |
| 4,158,023 A | 6/1979 | Von Halaaz |
| 4,766,260 A | 8/1988 | Manzer et al. |
| 4,843,181 A | 6/1989 | Gumprecht et al. |
| 4,902,838 A | 2/1990 | Manzer et al. |
| 5,036,036 A | 7/1991 | Lerou |
| 5,136,113 A | 8/1992 | Rao |
| 5,171,901 A | 12/1992 | Gassen et al. |
| 5,268,122 A | 12/1993 | Rao et al. |
| 5,563,304 A | 10/1996 | Rao et al. |

FOREIGN PATENT DOCUMENTS

| | | |
|---|---|---|
| CA | 515 661 | 8/1955 |
| CA | 2 073 533 | 1/1993 |
| FR | 2 384 734 | 10/1978 |
| GB | 902590 | 8/1962 |

OTHER PUBLICATIONS

Schotte, W., Ind. Eng. Chem., Process Des. Dev., 19, 432–439, 1980.
Tarrant, P., et al. Addition of Dibromodifluoromethane to Fluoroolefins, 2783–2787, May 20, 1955.
Haszeldine, R.N., et al., JCS Perkin, 1303–1307, 1974.

Primary Examiner—James O. Wilson
Assistant Examiner—Sikarl A. Witherspoon

(57) ABSTRACT

$CF_3CHFCHF_2$ production is disclosed which involves reacting $CF_3CF=CHF$ with HF at an elevated temperature over a catalyst selected from the group consisting of aluminum fluoride, fluorided alumina, metals supported on aluminum fluoride, metals supported on fluorided alumina and catalysts comprising trivalent chromium. Also disclosed is enrichment of $CF_3CF=CHF$ from a starting mixture containing $CF_3CF=CHF$ and $CF_3CH=CF_2$ which involves reacting said starting mixture with HF at an elevated temperature over a catalyst consisting essentially of carbon, a catalyst consisting essentially of metal halides supported on carbon, a catalyst consisting essentially of $Cr_2O_3$, or mixtures thereof (provided that when $Cr_2O_3$ is present the temperature is about 250° C. or less) to produce a product mixture containing $CF_3CH_2CF_3$ and unreacted $CF_3CF=CHF$ wherein the mole ratio of $CF_3CF=CHF$ to $CF_3CH=CF_2$ is greater than the ratio thereof in the starting mixture.

Compositions are disclosed which consist essentially of hydrogen fluoride in combination with an efective amount of a compound selected from the group consisting of $CF_3CHFCHF_2$ and $CF_3CH_2CF_3$ to form an azeotrope or azeotrope-like composition with hydrogen fluoride. Included are compositions containing from about 31 to 60 mole percent $CF_3CHFCHF_2$ and compositions containing from about 41 to 63 mole percent $CF_3CH_2CF_3$.

6 Claims, No Drawings

PRODUCTION OF 1,2-DIHYDRO AND 2,2-DIHYDRO HEXAFLUOROPROPANES AND AZEOTROPES THEREOF WITH HF

This application is a divisional application of, U.S. patent application Ser. No. 09/445,742, filed Dec. 10, 1999, now U.S. Pat. No. 6,386,147, which represents a national filing under 35 USC 371 of International Application No. PCT/US95/05862 filed May 19, 1995 and claims priority of U.S. patent application Ser. No. 08/249,405 filed May 26, 1994, now U.S. Pat. No. 5,563,304.

FIELD OF THE INVENTION

This invention relates to the manufacture of hydrofluorocarbons (i.e., HFCs) and azeotropic compositions thereof, and more particularly to the production of hexafluoropropanes and their azeotropic compositions with HF.

BACKGROUND 1,1,1,2,3,3-hexafluoropropane (i.e., $CHF_2CHFCF_3$ or HFC-236ea) and 1,1,1,3,3,3-hexafluoropropane (i.e., $CF_3CH_2CF_3$ or HFC-236fa) are useful as refrigerants, fire extinguishants, heat transfer media, gaseous dielectrics, sterilant carriers, polymerization media, particulate removal fluids, carrier fluids, buffing and abrasive agents, displacement drying agents and power cycle working fluids. In particular, HFC-236ea and HFC-236fa are highly effective as refrigerants for use in refrigeration equipment.

U.S. Pat. No. 5,171,901 discloses a process for the preparation of HFC-236fa by contacting a mixture of hexachloropropene and HF with a catalyst consisting of a mixture of $CrCl_3$ and $MgF_2$ at temperatures ranging from 350° C. to 500° C. The reaction temperatures and yields of HFC-236fa were as follows: 350° C., none detected; 400° C., 10%; 450° C., 55%; and 500° C., 64%. Other products formed in varying amounts were $CF_3CHClCF_3$, $CF_3CCl_2CF_3$, $CF_3CCl=CF_2$, $CF_3CCl=CClF$, and $CF_3CCl=CCl_2$. HFC-236ea has been prepared by the hydrogenation of hexafluoropropane. There is an interest in developing additional, efficient processes for the manufacture of HFC-236ea and HFC-236fa from various starting materials.

SUMMARY OF THE INVENTION

This invention provides a process for producing $CF_3CHFCHF_2$. This process comprises reacting $CF_3CF=CHF$ with HF at an elevated temperature over a catalyst selected from the group consisting of aluminum fluoride, fluorided alumina, metals supported on aluminum fluoride, metals supported on fluorided alumina and catalysts comprising trivalent chromium. Also provided is a process for enriching $CF_3CF=CHF$ from a starting mixture containing $CF_3CF=CHF$ and $CF_3CH=CF_2$. This process comprises reacting said starting mixture with HF at an elevated temperature over a catalyst consisting essentially of carbon, a catalyst consisting essentially of metal halides supported on carbon, a catalyst consisting essentially of $Cr_2O_3$, or mixtures thereof (provided that when $Cr_2O_3$ is present the temperature is about 250° C. or less) to produce a product mixture containing $CF_3CH_2CF_3$ and unreacted $CF_3CF=CHF$ wherein the mole ratio of $CF_3CF=CHF$ to $CF_3CH=CF_2$ is greater than the ratio thereof in the starting mixture. This invention provides for production of $CF_3CH_2CF_3$ (or both $CF_3CFHCHF_2$ and $CF_3CH_2CF_3$) by reacting a starting mixture containing both $CF_3CF=CHF$ and $CF_3CH=CF_2$ with HF at an elevated temperature over a fluorination catalyst.

This invention further provides compositions which consist essentially of hydrogen fluoride in combination with an efective amount of a compound selected from the group consisting of $CF_3CHFCHF_2$ and $CF_3CH_2CF_3$ to form an azeotrope or azeotrope-like composition with hydrogen fluoride, said composition containing from about 31 to 60 mole percent $CF_3CHFCHF_2$ or from about 41 to 63 mole percent $CF_3CH_2CF_3$.

DETAILED DESCRIPTION

The addition of hydrogen fluoride across the double bond of olefinic compounds normally follows. Markovnikov's rule (i.e., hydrogen is added to the carbon atom of the double bond which has a hydrogen atom, and fluorine to the olefinic carbon atom which has a fluorine atom). U.S. Pat. No. 5,268,122 provides examples of Markovnikov addition to olefinic fluoro-carbon bonds. In accordance with this invention, HF adds across the double bond of $CF_3CF=CHF$ to produce $CHF_2CHFCF_3$ rather than the Markovnikov expected product, $CH_2FCF_2CF_3$. Thus, this invention provides a process which involves reacting $CF_3CF=CHF$ with HF to add H at the olefinic carbon different from the olefinic carbon already containing a hydrogen such that $CF_3CFHCHF_2$ is produced.

$CF_3CF=CHF$ can be prepared according to R. N. Hazeldine et al., J. Chem. Soc. Perkin Trans.1, 1303-07 (1974). $CF_3CF=CHF$ may also be produced from $CF_3CF_2CH_2F$ (i.e., HFC-236cb) by dehydrofluorination (e.g., by reacting $CF_3CF_2CH_2F$ with KOH). Because of this unexpected chemistry, HFC-236cb can be converted to HFC-236ea by first dehydrofluorinating HFC-236cb to $CF_3CF=CHF$ and then reacting the $CF_3CF=CHF$ with HF to afford HFC-236ea. Accordingly, this invention provides a process for producing $CF_3CHFCHF_2$ from its isomer $CF_3CF_2CH_2F$ by dehydrofluorinating $CF_3CF_2CH_2F$ to $CF_3CF=CHF$, and reacting $CF_3CF=CHF$ with HF to provide $CF_3CHFCHF_2$.

Preferred catalysts for the reaction of $CF_3CF=CHF$ with HF include aluminum fluoride, fluorided alumina, metals supported on aluminum fluoride, metals supported on fluorided alumina and catalysts containing trivalent chromium. Suitable metals (including metal oxides, metal halides and/or other metal salts) for use on aluminum fluoride or fluorided alumina include (in addition to trivalent chromium) Group VIII metals (iron, cobalt, nickel, ruthenium, rhodium, palladium, osmium, iridium, platinum), Group VIIB metals (manganese, rhenium), Group IIIB metals (scandium, yttrium, lanthanum), Group IB metals (copper, silver, gold), zinc and/or metals having an atomic number of 58 through 71 (cerium, praseodymium, neodymium, promethium, samarium, europium, gadolinium, terbium, dysprosium, holmium, erbium, thulium, ytterbium, or lutetium). Preferably the total metal content of the catalyst will be from about 0.1 to 20 percent by weight; typically from about 0.1 to 10 percent by weight of the supported catalyst. It is understood that in catalyst preparation a metal compound may be supported on an alumina, and the resulting supported metal composition may then be fluorinated. Especially preferred for the reaction of $CF_3CF=CHF$ are chrome oxide catalysts prepared by the pyrolysis of ammonium dichromate (see U.S. Pat. No. 5,036,036 for preparative details).

Typically-the temperature for the reaction of $CF_3CF=CHF$ is from about 275° C. to 450° C. Temperatures between 300° C. and 400° C. are generally preferred.

A process for production of $CF_3CH_2CF_3$ is also provided by this invention. $CF_3CH_2CF_3$ may be produced by reacting $CF_3CH=CF_2$ in a starting mixture containing $CF_3CH=CF_2$ and $CF_3CF=CHF$ with HF to add H at the olefinic carbon already containing a hydrogen. Fluorination catalysts are used for this reaction. Preferably, the mole ratio of $CF_3CH=CF_2$ to $CF_3CF=CHF$ in the starting mixture is from 5:95 to 95:5.

Suitable catalysts which can be used for reacting $CF_3CH=CF_2$ with HF to produce $CF_3CH_2CF_3$ include vapor phase fluorination catalysts. Catalysts which may be used in accordance with this invention include metals (including metal oxides, metal halides and/or other metal salts); fluorided alumina; aluminum fluoride; metals on aluminum fluoride; metals on fluorided alumina; metals on carbon; and chromium catalysts. Suitable metals for use in such catalysts include chromium, Group VIII metals (iron, cobalt, nickel, ruthenium, rhodium, palladium, osmium, iridium, platinum), Group VIIB metals (manganese, rhenium), Group IIIB metals (scandium, yttrium, lanthanum), Group IB metals (copper, silver, gold), zinc and/or metals having an atomic number of 58 through 71 (cerium, praseodymium, neodymium, promethium, samarium, europium, gadolinium, terbium, dysprosium, holmium, erbium, thulium, ytterbium, or lutetium). Preferably when used on a support, the total metal content of the catalyst will be from about 0.1 to 20 percent by weight; typically from about 0.1 to 10 percent by weight.

Fluorided alumina and aluminum fluoride can be prepared as described in U.S. Pat. No. 4,902,838. Metals on aluminum fluoride and metals on fluorided alumina can be prepared by procedures described in U.S. Pat. No. 4,766,260. Catalysts comprising chromium are well known in the art, e.g., see U.S. Pat. No. 5,036,036. Chromium supported on alumina can be prepared as described in U.S. Pat. No. 3,541,165. Chromium supported on carbon can be prepared as described in U.S. Pat. No. 3,632,834. Preferred catalysts include aluminum fluoride, fluorided alumina, catalysts comprising carbon and catalysts comprising chromium oxide.

Typically, the temperature for the reaction of $CF_3CH=CF_2$ is from about 150° C. to 450° C. Temperatures between 175° C. and 400° C. are generally preferred. It is noted that suitable catalysts include those listed above for the reaction of $CF_3CF=CHF$ with HF. When these catalysts are used at sufficiently high temperatures, the product contains $CF_3CFHCHF_2$ along with $CF_3CH_2CF_3$.

In accordance with this invention, catalysts selected from the group consisting of (1) catalysts consisting essentially of carbon, (2) catalysts consisting essentially of metal halides supported on carbon, (3) catalysts consisting of $Cr_2O_3$, and mixtures thereof, may be used such that $CF_3CH=CF_2$ is selectively reacted with HF and the reaction product contains $CF_3CH_2CF_3$ and unreacted $CF_3CF=CHF$ from the starting mixture. Suitable metal halides include chlorides and fluorides of chromium, nickel, cobalt, zinc, copper, iron and/or manganese. Especially-preferred are carbon catalysts which have an ash content of less than about 0.1 percent by weight (see U.S. Pat. No. 5,136,113 for preparative details). The selective reaction of $CF_3CH=CF_2$ with HF may be used to provide enriched $CF_3CF=CHF$ from a mixture of $CF_3CF=CHF$ and $CF_3CH=CF_2$. The selective reaction of $CF_3CH=CF_2$ is normally conducted at a temperature within the range of about 150° C. to 350° C. (preferably between about 200° C. and 300° C.); except that when $Cr_2O_3$. is present the temperature should normally be about 250° C. or less.

If desired, the $CF_3CH_2CF_3$ produced by selective reaction of $CF_3CH=CF_2$ may be separated by conventional processes (e.g., distillation) from the unreacted $CF_3CF=CHF$, and the $CF_3CF=CHF$ may then be reacted with HF as described above to form $CF_3CHFCHF_2$ in an additional step. Accordingly, a process for producing $CF_3CHFCHF_2$ is provided which also produces $CF_3CH_2CF_3$ comprises reacting a starting mixture comprising $CF_3CH=CF_2$ and $CF_3CF=CHF$ with HF at an elevated temperature using a catalyst consisting essentially of carbon, a catalyst consisting essentially of metal halides supported on carbon, a catalyst consisting essentially of $Cr_2O_3$, or mixtures thereof (provided that when $Cr_2O_3$ is present the temperature is about 250° C. or less) to provide a product mixture containing $CF_3CH_2CF_3$ and unreacted $CF_3CF=CFH$; separating $CF_3CH_2CF_3$ from $CF_3CF=CHF$ in the product mixture; and reacting $CF_3CF=CHF$ from the product mixture with HF at an elevated temperature over a catalyst selected from the group consisting of aluminum fluoride, fluorided alumina, metals on aluminum fluoride, metals on fluorided alumina and catalysts containing trivalent chromium to produce $CF_3CHFCHF_2$. $CF_2=CHCF_3$ can be prepared according to P. Tarrant et 10 al., J. Am. Chem. Soc., 77, 2783-7 (1955).

It is noted that at temperatures of about 250° C. or less, $Cr_2O_3$ catalyst may be advantageously used for the selective reaction of $CF_3CH=CF_2$ from a mixture containing $CF_3CH=CF_2$ and $CF_3CF=CHF$ to provide a product mixture containing $CF_3CH_2CF_3$:and unreacted $CF_3CF=CHF$; whereas at higher temperatures $Cr_2O_3$ catalyst more readily provides reaction of both $CF_3CH=CF_2$ and $CF_3CF=CHF$. Accordingly, two reaction zones sequentially operating at a temperature of about 250° C. or less, and at a temperature above 250° C. may be used to sequentially convert $CF_3CH=CF_2$ and then $CF_3CF=CHF$.

The molar ratio of HF to the $C_3HF_5$ olefin or mixture of olefins being reacted typically ranges from about 1:1 to about 100:1, and is preferably within the range of about 1:1 to about 4:1. The contact time is typically from about 1 to about 100 seconds. 1,1,1,3,3,3-Hexafluoropropane and/or 1,1,1,2,3,3-hexafluoropropane may be recovered from the reaction products by using conventional techniques such as decantation and distillation.

The process of this invention can be carried out readily in the vapor phase using well known chemical engineering practice.

The reaction zone and its associated feed lines, effluent lines and associated units should be constructed of materials resistant to hydrogen fluoride.

Typical materials of construction, well-known to the fluorination art, include stainless steels, in particular of the austenic type, the well-known high nickel alloys, such as Monel® nickel-copper alloys, Hastelloy® nickel-based alloys and, Inconel® nickel-chromium alloys, and copper-clad steel. Also suitable for reactor fabrication are such polymeric plastics as polytrifluorochloroethylene and polytetrafluoroethylene, generally used as linings.

The present invention also provides compositions which consist essentially of hydrogen fluoride and an effective amount of a compound selected from $CF_3CH_2CF_3$ and $CHF_2CHFCF_3$ to form an azeotropic combination with hydrogen fluoride. By effective amount is meant an amount which, when combined with HF, results in the formation of an azeotrope or azeotrope-like mixture. As recognized in the art, an azeotrope or an azeotrope-like composition is an admixture of two or more different components which, when in liquid form under given pressure, will boil at a substantially constant temperature, which temperature may be higher or lower than the boiling temperatures of the individual components, and which will provide a vapor composition essentially identical to the liquid composition undergoing boiling.

An azeotrope is a liquid mixture that exhibits a maximum or minimum boiling point relative to the boiling points of surrounding mixture compositions. An azeotrope is homogeneous if only one liquid phase is present. An azeotrope is heterogeneous if more than one liquid phase is present. Regardless, a characteristic of minimum boiling azeotropes is that the bulk liquid composition is then identical to the vapor composition in equilibrium therewith, and distillation is ineffective as a separation technique. For the purpose of this discussion, azeotrope-like composition means a composition which behaves like an azeotrope (i.e., has constant-boiling characteristics or a tendency not to fractionate upon boiling or evaporation). Thus, the composition of the vapor formed during boiling or evaporation of such compositions is the same as or substantially the same as the original liquid composition. Hence, during boiling or evaporation, the liquid composition, if it changes at all, changes only to a minimal or negligible extent. This is to be contrasted with non-azeotrope-like compositions in which during boiling or evaporation, the liquid composition changes to a substantial degree.

Accordingly, the essential features of an azeotrope or an azeotrope-like composition are that at a given pressure, the boiling point of the liquid composition is fixed and that the composition of the vapor above the boiling composition is essentially that of the boiling liquid composition (i.e., no fractionation of the components of the liquid composition takes place). It is also recognized in the art that both the boiling point and the weight percentages of each component of the azeotropic composition may change when the azeotrope or azeotrope-like liquid composition is subjected to boiling at different pressures. Thus an azeotrope or an azeotrope-like composition may be defined in terms of the unique relationship that exists among components or in terms of the compositional ranges of the components or in terms of exact weight percentages of each component of the composition characterized by a fixed boiling point at a specified pressure. It is also recognized in the art that various azeotropic compositions (including their boiling points at particular pressures) may be calculated (see, e.g., W. Schotte, Ind. Eng. Chem. Process Des. Dev. 1980, 19, pp 432–439). Experimental identification of azeotropic compositions involving the. same components may be used to confirm the accuracy of such calculations and/or to modify the calculations for azeotropic compositions at the same or other temperatures and pressures.

Compositions may be formed which consist essentially of azeotropic combinations of hydrogen fluoride with a compound selected from $CF_3CH_2CF_3$ and $CHF_2CHFCF_3$. These include a composition consisting essentially of from about 40 to about 69 mole percent HF and from about 31 to 60 mole percent $CHF_2CHFCF_3$, (which forms an azeotrope boiling at a temperature from between about −25° C. and about 100° C. and a pressure between about 32 kPa and about 2500 kPa); and a composition consisting essentially of from about 37 to about 59 mole percent HF and from about 41 to about 63 mole percent $CF_3CH_2CF_3$ (which forms an azeotrope boiling at a temperature between about −25° C. and 100° C. and a pressure between about 44 kPa and about 2900 kPa).

At atmospheric pressure, the boiling points of hydrofluoric acid, HFC-236ea and HFC-236fa are about 19.5° C., 6° C. and −0.7° C., respectively. However, the relative volatility at 234 kPa (34 psia) and 20° C. of HF and HFC-236ea was found to be nearly 1.0 as 56 mole percent HF and 44 mole percent HFC-236ea was approached; and the relative volatility at 294 kPa (42.7 psia) and 20° C. of HF and HFC-236fa was found to be nearly 1.0 as 50 mole percent HF and 50 mole percent HFC-236fa was approached. These data indicate that the use of conventional distillation procedures will not result in the separation of a substantially pure compound because of the low value of relative volatility of the compounds.

To determine the relative volatility of HF with each of HFC-236ea and HFC-236fa, the so-called PTx Method was used. In this procedure, the total absolute pressure in a cell of known volume is measured at a constant temperature for various known binary compositions. use of the PTx Method is described in greater detail in "Phase Equilibrium in Process Design", Wiley-Interscience Publisher, 1970, written by Harold R. Null, on pages 124 to 126.

These measurements can be reduced to equilibrium vapor and liquid compositions in the cell by an activity coefficient equation model, such as the Non-Random, Two-Liquid (NRTL) equation, to represent liquid phase non-idealities. Use of an activity coefficient equation, such as the NRTL equation, is described in greater detail in "The Properties of Gases and Liquids", 4th Edition, publisher McGraw Hill, written by Reid, Prausnitz and Poling, on pages 241 to 387; and in "Phase Equilibria in Chemical Engineering", published by Butterworth Publishers, 1985, written by Stanley M.Walas, pages 165 to 244.

Without wishing to be bound by any theory or explanation, it is believed that the NRTL equation can sufficiently predict whether or not mixtures of HF and any of HFC-236ea and HFC-236fa behave in an ideal manner, and can sufficiently predict the relative volatilities of the components in such mixtures. Thus, while HF has a good relative volatility compared to HFC-236ea at low HFC-236ea concentrations, the relative volatility becomes nearly 1.0 as 44 mole percent HFC-236ea was approached at 20° C. This would make it impossible to separate HFC-236ea from HF by conventional distillation from such a mixture. Where the relative volatility approaches 1.0 defines the system as forming a near-azeotrope. Where the relative volatility is 1.0 defines the system as forming an azeotrope.

It has been found that azeotropes of HF and HFC-236ea are formed at a variety of temperatures and pressures. At a pressure of 34 psia (234 kPa) and 20° C., the azeotrope vapor composition was found to be about 56 mole percent HF and about 44 mole percent HFC-236ea. Based upon the above findings, it has been calculated that an azeotropic composition of about 69 mole percent HF and about 31 mole percent HFC-236ea can be formed at −25° C. and 4.7 psia (32 kPa) and an azeotropic composition of about 40 mole percent HF and about 60 mole percent HFC-236ea can be formed at 100° C. and 363 psia (2500 kPa). Accordingly, the present invention provides an azeotrope or azeotrope-like composition consisting essentially of from about 69 to 40 mole percent HF and from about 31 to 60 mole percent HFC-236ea, said composition having a boiling point from about −25° C. at 32 kPa to about 100° C. at 2500 kPa.

It has been found that azeotropes of HF and HFC-236fa are formed at a variety of temperatures and pressures. At a pressure of 42.7 psia (about 294 kPa) and 20° C., the azeotrope vapor composition was found to be about 50 mole percent HF and about 50 mole percent HFC-236fa. Based upon the above findings, it has been calculated that an azeotropic composition of about 37 mole percent HF and about 63 mole percent HFC-236fa can be formed at 100° C. and 422 psia (2900 kPa) Accordingly, the present invention provides an azeotrope or azeotrope-like composition consisting essentially of from about 59 to 37 mole percent HF and from about 31 to 63 mole percent HFC-236fa, said composition having a boiling point from −25° C. at about 44 kPa to about 100° C. at about 2900 kPa.

The HFC-236ea/HF and HFC-236fa/HF azeotropes are useful as feed to produce HFC-227ca ($CHF_2CF_2CF_3$) and/or HFC-227ea ($CF_3CHFCF_3$) (see U.S. Pat. No. 5,177,273). It will also be apparent to one of ordinary skill in the art that distillation including azeotropes with HF can typically be run under more convenient conditions than distillation without HF (e.g., where HF is removed prior to distillation).

Practice of the invention will become further apparent from the following non-limiting examples.

EXAMPLES

General Evaluation Procedure

A reactor, 11" (27.9 cm)×½" (1.3 cm) Inconel® nickel alloy tube, containing an internal thermowell, containing from about 12 to 15 mL of catalyst (10 to 14 mesh, i.e., about 1.7 to 1.3 mm), was heated in a fluidized sandbath. The feed to the reactor was measured through mass flow controllers. The organic feed was mixed with HF prior to entering the reactor. All examples were performed at ambient pressure. The products from the reactor were analyzed by on line GC/MS. The gas chromatograph was a Hewlett Packard HP 5890 containing a 20 foot (6.1 m) long, one-eighth inch (0.32 cm) diameter column containing Krytox®, a perfluorinated polyether on an inert support. The helium flow rate was 35 mL/minute. GC results are reported in mole %.

Activation of Carbon-based Catalysts

The reactor was charged with the catalyst and heated to 300° C. in a flow of nitrogen (25 mL/min) for about 2 hours. The temperature was reduced to 175° C. and a 2:1 molar ratio of nitrogen and HF was started through the reactor (total flow 100 mL/min). After about one hour under these conditions, the molar ratio of nirogen to HF was adjusted to 1:3 and the temperature gradually increased-over a two hour period to 400° C. The reactor was then brought to the desired operating temperature, the nitrogen flow stopped, and the flow of reactants started.

Activation of Chromium Oxide

The reactor was charged with chromium oxide and heated to about 175° C. for about two hours in a flow of nitrogen (25 mL/min). At the end of this period, a flow of nitrogen and HF in the molar ratio of 2:1 (total flow 100 mL/min) was started through the reactor. After an initial exotherm of about 10 to 30 degrees subsided, the molar ratio of nitrogen to HF was adjusted to 1:3 and the temperature gradually increased over a three hour period to 400° C. The reactor and contents were kept at this temperature for about an additional 30 minutes and brought back to the desired operating temperature. The nitrogen flow was stopped and the flow of reactants started.

EXAMPLE 1

Reaction of $CF_3CF$=$CFH$ with HF

The reactor was charged with 19.5 g of chromium oxide which was activated according to the procedure described above. A flow of HF and $CF_3CF$=$CFH$ in a 4:1 molar ratio was started through the reactor. The contact time was 30 seconds. The organic feed contained 85.3% $CF_3CF$=$CFH$ and 13.6% trifluoroethylene in addition to small amounts of other components. Product analysis indicated the following.

| Temp. ° C. | $CF_3CH_2F$ | $CF_3CF$=$CFH$ | $CF_3CHFCHF_2$ |
|---|---|---|---|
| 300 | 15.1 | 35.1 | 46.9 |
| 325 | 14.9 | 50.8 | 32.3 |

$CF_3CF$=$CFH$ is a mixture of cis and trans isomers. Small amounts of other byproducts were present.

EXAMPLE 2

Reaction of $CF_3CF$=$CFH$ with HF

The reactor was charged with 15.2 g of fluorided which was obtained by the exhaustive flourination of gamma-alumina with HF as described in U.S. Pat. No. 4,766,260. A flow of HF and $CF_3CF$=$CFH$ molar ratio was started through the reactor. The contact time was 30 seconds. The organic feed contained 85.3% $CF_3CF$=$CFH$, 13.6% trifluoroethylene and 0.8% $CF_3CFHCHF_2$ in addition to small amounts of other components. Product analysis indicated the following.

| Temp. ° C. | $CF_3CH_2F$ | $CF_3CF$=$CFH$ | $CF_3CHFCHF_2$ |
|---|---|---|---|
| 250 | 14.0 | 85.1 | 0.8 |
| 300 | 14.0 | 74.8 | 1.0 |
| 350 | 13.6 | 80.9 | 4.9 |
| 400 | 13.4 | 78.4 | 6.8 |
| 425 | 13.9 | 79.4 | 4.5 |

Small amounts of other byproducts were present.

EXAMPLE 3

Reaction of a Mixture of $CF_3CH$=$CF_2$ and $CF_3CF$=$CFH$ with HF

The reactor was charged with 6.3 g of acid washed carbon. It was dried in a stream of nitrogen (25 mL/min) for about two hours at 175° C. prior to start of the reaction. The organic feed mixture consisted of 47.3% $CF_3CH$=$CF_2$, 50.0% $CF_3CF$=$CFH$, 0.7% $CF_3CFHCHF_2$ and 0.4% $CF_3CH_2F_3$ in addition to small quantities of other products. The HF to total organic ratio was 4:1 and the contact time was 15 seconds. Product analysis indicated the following.

| Temp. ° C. | $CF_3CH$=$CF_2$ | $CF_3CF$=$CFH$ | $CF_3CFHCHF_2$ | $CF_3CH_2CF_3$ |
|---|---|---|---|---|
| 200 | 33.8 | 50.1 | 1.0 | 13.5 |
| 250 | 0.7 | 48.4 | 1.0 | 46.0 |

EXAMPLE 4

Reaction of a Mixture of $CF_3CH$=$CF_2$ and $CF_3CF$=$CFH$ with HF

The reactor was charged with 6.5 g of 10 weight percent chromium chloride on carbon which was activated according to the general procedure described above. The organic feed mixture consisted of 47.3% $CF_3CH=CF_2$, 50.0% $CF_3CF=CFH$, 0.7% $CF_3CFHCHF_2$ and 0.4% $CF_3CH_2CF_3$ in addition to small quantities of other products. The HF to total organic ratio was 4:1 and the time was 15 seconds. Product analysis indicated the following.

| Temp. °C. | $CF_3CH=CF_2$ | $CF_3CF=CFH$ | $CF_3CFHCHF_2$ | $CF_3CH_2CF_3$ |
|---|---|---|---|---|
| 175 | 41.6 | 49.9 | 1.1 | 6.0 |
| 200 | 25.6 | 49.1 | 1.6 | 21.9 |
| 225 | 7.2 | 48.3 | 2.0 | 40.5 |
| 250 | 1.0 | 46.4 | 2.3 | 48.6 |

EXAMPLE 5

Reaction of a Mixture of $CF_3CH=CF_2$ and $CF_3CF=CFH$ with HF

The reactor was charged with 19.4 g of chromium oxide which was activated with HF according to the general procedure described above. The organic feed mixture consisted of 47.4% $CF_3CH=CF_2$, 50.1% $CF_3CF=CFH$, 0.7% $CF_3CFHCHF_2$ and 0.4% $CF_3CH_2CF_3$ in addition to small quantities of other products. The HF to total organic ratio was 4:1 and the contact time was 15 seconds. Product analysis indicated the following.

| Temp. °C. | $CF_3CH=CF_2$ | $CF_3CF=CFH$ | $CF_3CFHCHF_2$ | $CF_3CH_2CF_3$ |
|---|---|---|---|---|
| 125 | 45.6 | 50.4 | 1.0 | 2.1 |
| 150 | 37.7 | 50.2 | 1.3 | 9.9 |
| 175 | 8.6 | 49.0 | 3.6 | 37.9 |
| 200 | 0.1 | 46.2 | 4.5 | 48.1 |
| 225 | 0.0 | 46.2 | 4.6 | 48.4 |
| 250 | 0.0 | 45.6 | 4.8 | 48.3 |
| 279 | 0.0 | 43.3 | 6.8 | 48.4 |
| 302 | 0.0 | 36.1 | 13.6 | 48.3 |
| 326 | 0.0 | 29.1 | 19.5 | 49.3 |
| 350 | 0.0 | 33.6 | 15.8 | 48.4 |

There were small amounts of other minor by-products present.

Examination of the data shown in Example 5 indicates that reaction at a lower temperature produces $CF_3CH_2CF_3$ and reaction at a higher temperature produces $CF_3CFHCHF_2$ thus showing that the same catalyst can be used in a two stage reaction, one stage operating at a lower temperature and one stage operating at a higher temperature.

What is claimed is:

1. A process for producing $CF_3CHFCHF_2$, comprising:

reacting $CF_3CF=CHF$ with HF at an elevated temperature over a catalyst selected from the group consisting of aluminum fluoride, fluorided alumina, metals on aluminum fluoride, metals on fluorided alumina and catalysts comprising trivalent chromium.

2. The process of claim 1 wherein $CF_3CF=CHF$ is produced by dehydrofluorinating $CF_3CF_2CH_2F$.

3. The process of claim 1 wherein a starting mixture comprising $CF_3CF=CHF$ and $CF_3CH=CF_2$ is reacted with HF at an elevated temperature over a fluorination catalyst to produce $CF_3CH_2CF_3$ from said $CF_3CH=CF_2$.

4. The process of claim 3 wherein the starting mixture is reacted at an elevated temperature over a catalyst consisting essentially of carbon, a catalyst consisting essentially of metal halides on carbon, a catalyst consisting essentially of $Cr_2O_3$, or mixtures thereof, provided that when $Cr_2O_3$ is present the temperature is about 250° C. or less, to provide a product mixture containing $CF_3CH_2CF_3$ and unreacted $CF_3CF=CFH$; wherein the $CF_3CH_2CF_3$ is separated from $CF_3CF=CHF$ in the product mixture; and wherein $CF_3CF=CHF$ from the product mixture is reacted with HF.

5. The process of claim 4 wherein the starting mixture is reacted with HF over a catalyst consisting essentially of carbon.

6. The process of claim 4 where $CF_3CF=CHF$ from the product mixture is reacted with HF over chromium oxide prepared by the pyrolysis of ammonium dichromate.

* * * * *